US010132816B2

(12) United States Patent
Maratos-Flier et al.

(10) Patent No.: US 10,132,816 B2
(45) Date of Patent: Nov. 20, 2018

(54) MEASUREMENT OF FGF21 AS A BIOMARKER OF FRUCTOSE METABOLISM

(71) Applicant: Beth Israel Deaconess Medical Center, Inc., Boston, MA (US)

(72) Inventors: Eleftheria Maratos-Flier, Newton, MA (US); Mark Herman, Needham, MA (US); Jody Dushay, Newton, MA (US); Ffolliott Martin Fisher, Watertown, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 77 days.

(21) Appl. No.: 14/774,625

(22) PCT Filed: Mar. 13, 2014

(86) PCT No.: PCT/US2014/025527
§ 371 (c)(1),
(2) Date: Sep. 10, 2015

(87) PCT Pub. No.: WO2014/159961
PCT Pub. Date: Oct. 2, 2014

(65) Prior Publication Data
US 2016/0033534 A1    Feb. 4, 2016

Related U.S. Application Data

(60) Provisional application No. 61/781,675, filed on Mar. 14, 2013.

(51) Int. Cl.
| | |
|---|---|
| *G01N 30/02* | (2006.01) |
| *G01N 30/72* | (2006.01) |
| *G01N 33/53* | (2006.01) |
| *G01N 33/68* | (2006.01) |
| *G01N 33/74* | (2006.01) |
| *C12Q 1/6883* | (2018.01) |

(52) U.S. Cl.
CPC ....... *G01N 33/6893* (2013.01); *C12Q 1/6883* (2013.01); *G01N 33/74* (2013.01); *C12Q 2600/158* (2013.01); *G01N 2333/50* (2013.01); *G01N 2333/575* (2013.01); *G01N 2800/04* (2013.01)

(58) Field of Classification Search
None
See application file for complete search history.

(56) References Cited

FOREIGN PATENT DOCUMENTS

WO    WO 2010/109066 A1    9/2010

OTHER PUBLICATIONS

Lin et al. (J. Clin. Endocrinol. Metab. 97: E1224-E1228, 2012).*
International Preliminary Report on Patentability and the Written Opinion for PCT/US2014/025527, "Measurement of FGF21 as a Biomarker of Fructose Metabolism and Metabolic Disease", dated Sep. 24, 2015.
Badman, M.K., et al., "Hepatic Fibroblast Growth Factor 21 is Regulated by PPARα and is a Key Mediator of Hepatic Lipid Metabolism in Ketotic States", *Cell Metabolism*, 5: 426-437 (2007).
Dushay, J., et al., "The FGF21 Response to Fructose in Humans: Defining a Fructose Tolerance Test", 73 American Diabetes Associateion Scientific Sessions, Jun. 21-25, 2013 Chicago, IL, Abstract No. 159-LB: 3 pages.
Kharitonenkow, A., et al., "FGF-21 as a Novel Metabolic Regulator", *J. Clin. Invest.*, 115: 1627-1635 (2005).
Iglesias, P., et al., "Biological Role, Clinical Significance, and Therapeutic Possibilities of the Recently Discovered Metabolic Hormone Fibroblastic Growth Factor 21", *European Journal of Endocrinology*, 167: 301-309 (2012).
Woo, Y.C., et al., "Fibroblast Growth Factor 21 as an Emerging Metabolic Regulator: Clinical Perspectives", *Clinical Endocrinology*, 78: 489-496 (2013).

* cited by examiner

*Primary Examiner* — Christine J Saoud
(74) *Attorney, Agent, or Firm* — Hamilton, Brooks, Smith & Reynolds, P.C.

(57) ABSTRACT

The invention provides, inter alia, methods of monitoring the fructose response of a subject by determining the level of fibroblast growth factor 21 (FGF21) gene expression product in a biological sample (such as a serum sample) from the subject, where the subject was previously administered a fructose bolus. The invention also provides methods of monitoring the response of a subject to a treatment for a disorder of metabolism, for discriminating fructose intolerance from other gastrointestinal disorders not associated with fructose intolerance, for identifying a subject at risk for developing a disorder of metabolism, as well as methods of treatment for a disorder of metabolism.

7 Claims, 5 Drawing Sheets

MEASUREMENT OF FGF21 AS A BIOMARKER OF FRUCTOSE METABOLISM

RELATED APPLICATION

This application is the U.S. National Stage of International Application No. PCT/US2014/025527, filed Mar. 13, 2014, which designates the U.S., published in English, and claims the benefit of U.S. Provisional Application No. 61/781,675, filed on Mar. 14, 2013. The entire teachings of the above application are incorporated herein by reference.

BACKGROUND OF THE INVENTION

The metabolic syndrome is a cluster of disorders that includes obesity, hypertriglyceridemia, hypertension, non-alcoholic fatty liver disease (NAFLD), impaired glucose metabolism, and insulin resistance all of which contribute to increased risk for the development of diabetes and cardiovascular disease[1-4]. The concept of a metabolic syndrome was popularized by Gerald Reaven in the 1980s who postulated that a common pathogenic mechanism must lay at the heart of these diverse conditions by demonstrating that a single dietary intervention, high-fructose feeding, can reproduce all the features of the syndrome in rodents[5]. Epidemiologic data indicate that increased sugar consumption is a major contributor to the development of the metabolic syndrome including obesity and diabetes[6]. Increased consumption of sugar-sweetened beverages accounts for the majority of the increase in sugar ingestion[7]. Sugar is a disaccharide composed of one glucose and one fructose molecule. The fructose component of sugar is particularly harmful. Prospective clinical experiments demonstrate that increased fructose ingestion, but not increased glucose ingestion, promotes dyslipidemia, increases visceral adiposity, and impairs insulin sensitivity in human subjects[8]. Studies also suggest that increased sugar or fructose consumption also contributes to the development of Non-Alcoholic Fatty Liver Disease (NAFLD)[9]. The mechanisms by which high-sugar or high-fructose feeding cause metabolic dysfunction remain unclear. Furthermore a specific, quantifiable acute biologic response to fructose ingestion has never been defined.

In view of the prevalence of metabolic syndrome and associated disorders of metabolism, the role of fructose in the development or complications of these disorders, and the absence of a specific quantifiable biologic response to fructose ingestion, a need exists for methods of monitoring the fructose response in a subject.

SUMMARY OF THE INVENTION

The invention provides, inter alia, methods of monitoring the fructose response in a subject.

In a first aspect, the invention provides methods of monitoring the fructose response in a subject by determining a level of a fibroblast growth factor 21 (FGF21) gene expression product in an isolated biological sample obtained from the subject, where the subject was previously administered a fructose bolus. Any suitable biological sample may be used, including blood or a fraction thereof, such as plasma or serum; urine; sweat; mucus; lymphatic fluid; saliva; cerebrospinal fluid; or a tissue biopsy (e.g., liver or subcutaneous adipose tissue).

In some embodiments, the level of FGF21 gene expression product is determined at the protein level. In particular embodiments, the level of FGF21 protein gene expression product is determined by ELISA, Western Blotting, RIA (radioimmunoassay), nucleic acid-based or protein-based aptamer techniques, HPLC (high precision liquid chromatography), SPR (surface plasmon resonance), SAT (suspension array technology), direct peptide sequencing, or mass spectrometry. In still more particular embodiments, the level of FGF21 protein gene expression product is determined using an antibody, or antigen-binding fragment thereof, that specifically binds FGF21. In still more particular embodiments, the antibody is detectably labeled. And in other particular embodiments, the level of FGF21 protein gene expression product is determined by ELISA.

In certain embodiments, the level of FGF21 gene expression product is determined at the nucleic acid level. In particular embodiments, the isolated biological sample is a biopsy comprising liver tissue or subcutaneous adipose tissue. In more particular embodiments, the level of nucleic acid FGF21 gene expression product is determined by microarray, quantitative polymerase chain reaction (qPCR), quantitative real-time polymerase chain reaction (qRTPCR), sequencing, northern blotting, digital drop PCR (ddPCR), or Southern blotting.

In a related aspect, the invention provides methods of monitoring the fructose response in a subject by administering a fructose bolus to the subject and determining a circulating level of a fibroblast growth factor 21 (FGF21) protein gene expression product in an isolated serum sample obtained from the subject, within about 0.5 to about 4 hours of administering the fructose bolus, where a basal level of circulating FGF21 protein gene expression product in an isolated serum sample obtained from the subject was determined before administering the fructose bolus to the subject.

In particular embodiments of any of the foregoing aspects or embodiments, the subject is undergoing treatment with a ketohexokinase inhibitor, a biguanidine, a GLP1/GLP1R agonist, peroxisome proliferator-activated receptors (PPAR) agonist, an Sglt2 inhibitor, omega-3 fatty acids, omega-6 fatty acids, ketohexokinase (fructokinase) activator or inhibitor, an aldolase b (Aldob) activator or inhibitor, a triokinase activator or inhibitor, a Slc2a2 (Glut2) activator or inhibitor, a Slc2a5 (Glut5) activator or inhibitor, a glucokinase (Gck) activator, a Gck inhibitor, an agent that stabilizes the inhibitory interaction between Gck and Gckr, a glucosidase inhibitor, an activator or inhibitor of a transporter or enzyme involved in fructose and/or carbohydrate metabolism, or a combination thereof.

In another aspect, the invention provides methods of evaluating the effect of a metabolic treatment regimen in a subject undergoing the treatment regimen, by determining a level of a fibroblast growth factor 21 (FGF21) gene expression product in an isolated biological sample obtained from the subject, wherein the subject was previously administered a fructose bolus. In particular embodiments, the metabolic treatment regimen comprises the use of a test composition. In more particular embodiments, the test composition comprises a ketohexokinase inhibitor, a biguanidine, a GLP1/GLP1R agonist, peroxisome proliferator-activated receptors (PPAR) agonist, an Sglt2 inhibitor, omega-3 fatty acids, omega-6 fatty acids, ketohexokinase (fructokinase) activator or inhibitor, an aldolase b (Aldob) activator or inhibitor, a triokinase activator or inhibitor, a Slc2a2 (Glut2) activator or inhibitor, a Slc2a5 (Glut5) activator or inhibitor, a glucokinase (Gck) activator, a Gck inhibitor, a glucosidase inhibitor an agent that stabilizes the inhibitory interaction between Gck and Gckr, an activator or inhibitor of a transporter or enzyme involved in fructose and/or carbohydrate metabolism, or a combination thereof. In other particular embodiments, the treatment regimen is for treating metabolic syndrome.

In some more particular embodiments of any of the forgoing aspects or embodiments, the subject may be determined to be at increased risk for developing a disorder of metabolism on the basis of detecting an aberrant fructose response by the methods provided by the invention.

In another aspect, the invention provides methods of discriminating between a diagnosis of fructose intolerance versus a diagnosis of a gastrointestinal disorder that is not associated with fructose intolerance in a subject exhibiting symptoms of a gastrointestinal symptoms and/or malabsorption, by determining the fructose response of the subject by the method of any one of the methods provided by the invention, where, for example, detecting an aberrant fructose response in the subject identifies the subject as having fructose intolerance and detecting a normal fructose response identifies the subject as having a gastrointestinal disorder that is not associated with fructose intolerance.

In another aspect, the invention provides methods of identifying a subject at risk for developing a disorder of metabolism by determining a basal level of a circulating fibroblast growth factor 21 (FGF21) protein gene expression product in an isolated serum sample obtained from the subject, administering a fructose bolus to the subject, determining a level of a circulating FGF21 protein gene expression product in an isolated serum sample obtained from the subject within about 0.5 to about 4 hours of administering the fructose bolus and evaluating the change in circulating FGF21 protein gene expression product levels determined after administration of the fructose bolus, relative to the basal level, where a change in circulating FGF21 protein gene expression product levels more than, for example, about two standard deviations from a normal control identifies the subject as being at risk for developing a disorder of metabolism.

In more particular embodiments of any of the foregoing aspects and embodiments, the subject is determined to be at risk for developing a disorder of metabolism on the basis of an aberrant fructose response, and the methods further include the step of implementing a suitable therapy to the subject to treat the disorder of metabolism, where, in some embodiments, the suitable therapy is selected from change in diet, change in exercise, discontinuing a medical treatment, starting a new medical treatment, modifying an existing medical treatment, or a combination thereof.

In another aspect, the invention provides a method of treating a disorder of metabolism in a subject by implementing a suitable therapy for the subject on the basis of detecting an aberrant fructose response in the subject by any one of the methods provided by the invention. In more particular embodiments, the suitable therapy is selected from change in diet, change in exercise, discontinuing a medical treatment, starting a new medical treatment, modifying an existing medical treatment, or a combination thereof.

In more particular embodiments of any of the foregoing aspects and embodiments, the subject is a mammal, e.g., a human, e.g., a human that has, or is at increased risk of developing, a disorder of metabolism.

In more particular embodiments of any of the foregoing aspects and embodiments, the fructose bolus comprises about 20 to about 100 grams of fructose.

In more particular embodiments of any of the foregoing aspects and embodiments, the level of a FGF21 gene expression product is determined within about 0.5 to about 4 hours of administering the fructose bolus.

In more particular embodiments of any of the foregoing aspects and embodiments, the methods further include determining a level of a FGF21 gene expression product before administering the fructose bolus.

In more particular embodiments of any of the foregoing aspects and embodiments, a time series of at least 2, 3, 4, or 5 levels of FGF21 gene expression product is determined for the subject.

In more particular embodiments of any of the foregoing aspects and embodiments, the level of FGF21 gene expression product is evaluated as the ratio of peak to baseline, difference between peak and baseline FGF21, total area under the curve, incremental area under the curve, total area under the curve following the peak, incremental area under the curve following the peak, or time for decrease to about ½ peak value.

In another aspect, the invention provides a suitable therapeutic for a disorder of metabolism for use in treating a subject determined to exhibit an aberrant fructose response by any one of the methods provided by the invention.

In another aspect, the invention provides use of a suitable therapeutic for a disorder of metabolism in the preparation of a medicament for treating a subject determined to exhibit an aberrant fructose response by the method of any one of the methods provided by the invention.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2A-2B show plasma FGF21 levels: FIG. 2A) following ingestion of 75 grams glucose (n=8) and FIG. 2B) Plasma FGF21 levels following ingestion of 75 grams fructose in human subjects (n=10).

DETAILED DESCRIPTION OF THE INVENTION

A description of example embodiments of the invention follows.

Certain Definitions

"Gene expression product" encompasses both nucleic acid (e.g., mRNA or cDNA derived from it) and protein products of expression of a gene. Nucleic acid expression products may or may not include subsequences that do not encode and/or get translated into protein. Gene expression product encompass both full-length, naturally occurring molecules, as well as fragments thereof, provided the fragments permit identification of the gene expression product, relative to other molecules expected to be present in the sample being analyzed.

"Determining" a level of a gene expression product, such as an FGF21 gene expression product, requires contacting a sample with isolated analytic tools, such as laboratory equipment for measuring the level, and, in certain embodiments, additional isolated reagents, such as isolated oligonucleotides, microarrays, sequencing reagents (such as cloned enzymes, detectably labeled dNTPs, et cetera), antibodies (including antigen-binding fragments thereof; optionally where the antibody or antigen-binding fragment thereof is detectably labeled) to measure the level of a gene expression product by an analytical laboratory method. Determining a level of a gene expression product may be done directly in the course of the analytical laboratory methods or, in some embodiments, by evaluating the quantitative output of the analytical laboratory methods.

"Level of expression," "expression level," "gene expression level" and the like, refers to the amount of a gene expression product (e.g., mRNA or protein) and may be normalized by any suitable means.

"Fructose bolus" is a quantity of fructose-containing carbohydrate compound that provides fructose (see, e.g., CAS 57-48-7, PubChem 134970870; fructose also encompasses isotopic variants of the naturally-occurring monosaccharide) to the blood of the subject to which it is administered. Administration of a fructose bolus is also known as a "fructose challenge."

"Administering," "administered," "administration" and the like, in the context of a fructose bolus, comprises both direct administration by, e.g. intravenous administration by a medical professional as well as providing a fructose bolus to the subject, e.g. giving a fructose bolus, such as an oral form fructose bolus, to the subject with instructions to self-administer it, or otherwise instructing the subject to obtain and administer a suitable fructose bolus.

"Circulating level" is a level (e.g. of a FGF21 gene expression product) detectable in the blood, or a fraction thereof, such as serum or plasma.

"Disorder of metabolism" encompasses obesity, "fatty liver disease" (including steatosis, steatohepatitis, cirrhosis, and hepatocellular carcinoma), dyslipidemia including hypertriglyceridemia, low HDL cholesterol, elevated LDL cholesterol, and Hypertension, ketohexokinase deficiency and "diabetes-related disorders," which include type 2 diabetes (including complications of diabetes and metabolic disease including diabetic microvascular complications (nephropathy, neuropathy, retinopathy) and macrovascular complications (coronary artery disease, cerebrovascular disease, peripheral vascular disease and other atherosclerotic diseases)), MODY (including MODY1, MODY2, MODY3, MODY4, MODY5, MODY6, MODY7, MODY8, MODY9, MODY10, MODY11), impaired fasting glucose, impaired glucose tolerance, insulin resistance, metabolic syndrome glycogen storage diseases (including von Gierke's disease) and other genetic/enzymatic defects in carbohydrate metabolism.

"Fructose intolerance" includes Hereditary Fructose Intolerance (see OMIM 229600), and, in some embodiments, Essential Fructosuria (see OMIM 229800).

"Gastrointestinal disorder that is not associated with fructose intolerance" may include irritable bowel diseases or inflammatory bowel diseases, including Crohn's disease, ulcerative colitis, and gluten enteropathy/celiac disease lactose intolerance, as well as some forms of idiopathic irritable bowel that manifest with bloating, gas, and diarrhea.

"Highly stringent hybridization" means hybridization conditions comprising about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

FGF21

The methods provided by the invention typically entail determining the level of a fibroblast growth factor 21 (FGF21) gene expression product in a biological sample from the subject. Any portion of an FGF21 gene expression product may be suitable for detection, provided it sufficiently identifies the gene expression product relative to other materials expected to be present in the biological sample. Exemplary FGF21 protein and nucleic acid sequences are provided in Table A, below:

| Organism | GeneID | Ref mRNA | Ref Protein | Homologene |
|---|---|---|---|---|
| Homo sapiens | 26291 | NM_019113.2 | NP_061986.1 | 10428 |
| Mus musculus | 56636 | NM_020013.4 | NP_064397.1 | 10428 |
| Rattus norvegicus | 170580 | NM_130752.1 | NP_570108.1 | 10428 |

Additional FGF21 protein sequences are available for a variety of organisms, including P. troglodytes (XP_524333.1), M. mulatta (XP_001114178.2), C. lupus (XP_541510.2), and B. taurus (XP_002695246.1).

"Determining a level of a fibroblast growth factor 21 gene expression product" or "determining a level of a FGF21 gene expression product" is a dynamic (i.e. both before and following a fructose bolus) measurement of the amount of a FGF21 gene expression product and encompasses both measurement at a single timepoint, as well as multiple measurements—such as a time series of at least 2, 3, 4, 5, or more measurements. A "time series" is a group of 2 or more determined levels of FGF21 gene expression product relative to a fructose bolus—e.g. a series of pre-bolus and/or post-bolus measurements. Measurement(s) may be analyzed as absolute measurements of concentration or may be transformed, e.g., log normalized; normalized as a difference or fold change, e.g. between baseline and peak (relative maximum) in the same series of measurement or relative to another time (e.g. a pre-bolus baseline measurement from another time series for the subject, or a reference standard, e.g., either pre or post bolus reference standards); total or incremental area under the curve (AUC); total or incremental AUC after peak levels; or time (or rate) to increase (or decrease) to (from) a peak level, or some fraction thereof, e.g. 95, 90, 80, 70, 60, 50, 40, 30, 20, 10, or 5%, and in particular embodiments about 50% of peak level. The determined level(s) or transformed level(s) of a fibroblast growth factor 21 gene expression product is the subjects "fructose response."

"Aberrant fructose response" means fructose response that exhibits a significant (practical and/or statistical) deviation (temporal and/or quantitative) from suitable controls, such as established norms exemplified in the application, for measured levels of a FGF21 gene expression product (by any means of determining a level of a fibroblast growth factor 21 gene expression product, as defined herein). For example, aberrant fructose responses encompass levels of FGF21 gene expression products that are higher or lower than predicted following a fructose bolus, as well as fructose responses that are slower or faster than suitable controls, e.g., in some embodiments, by 1.5, 2.0, 2.5, 3.0 standard deviations, or more.

FGF21 gene expression product levels can be determined at either the protein or nucleic acid level by any suitable means known in the art. For example, for measuring FGF21 levels at the protein level, the level of FGF21 protein gene expression product may be determined by ELISA, Western Blotting, RIA (radioimmunoassay), nucleic acid-based or protein-based aptamer techniques, HPLC (high precision liquid chromatography), SPR (surface plasmon resonance), SAT (suspension array technology—including both immune-based, aptamer-based, or combination methods), direct peptide sequencing (such as Edman degradation sequencing), or mass spectrometry (such as MS/MS, optionally coupled to HPLC), In particular embodiments, the level of a FGF21 protein gene expression product is determined by ELISA.

Any suitable fragment of a FGF21 protein gene expression product (e.g. those described in Table A above) or a sequence substantially similar thereto, e.g., at least about 60, 65, 70, 75, 80, 85, 90, 95, 96, 97, 98, 99% or more homologous (i.e., conservative substitutions (see, e.g., Heinkoff and Heinkoff $PNAS$ 89 (22): 10915-10919 (1992) and Styczynski et al., $Nat. Biotech.$ 26 (3): 274-275 (BLOSUM, e.g., BLOSUM 45, 62 or 80) or Dayhoff et al., $Atlas of protein sequence and structure$ (volume 5, supplement 3 ed.), $Nat. Biomed. Res. Found.$ pp. 345-358 (PAM, e.g., PAM 30 or 70)) or identical at the amino acid level over a length of at least about 10, 20, 40, 60, 80, 100, 150, 200 or more amino acids or over the entire length of the FGF21 protein gene expression product, may be a suitable analyte in the methods provided by the invention. Fragments of FGF21 protein gene expression products—or similar peptide sequences—can be of any length sufficient to distinguish the fragment from other sequences expected to be present in a mixture, e.g., at least 5, 10, 20, 40, 60, 80, 100, 150, 200 or more amino acids or at least about 5, 10, 20, 30, 40, 50, 60, 70, 80, 90, 95% of the length of the FGF21 protein gene expression product.

Many of the modalities for determining the level of an FGF21 protein gene expression product employ antibodies. "Antibody," "antibodies," and the like, as used herein, refers to an immunoglobulin or a part thereof, and encompasses any polypeptide comprising an antigen binding site regardless of the source, species of origin, method of production, and characteristics. As a nonlimiting example, the term "antibody" includes human, orangutan, mouse, rat, goat, rabbit, sheep, and chicken antibodies. The term includes but is not limited to polyclonal, monoclonal, monospecific, polyspecific, nonspecific, humanized, camelized, singlechain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen binding function. Antibodies also include antigen-binding molecules that are not based on immunoglobulins, as further described below.

Antibodies can be made, for example, via traditional hybridoma techniques (Kohler and Milstein, $Nature$ 256: 495499 (1975)), recombinant DNA methods (U.S. Pat. No. 4,816,567), or phage display techniques using antibody libraries (Clackson et al., $Nature$ 352: 624628 (1991); Marks et al., $J. Mol. Biol.$ 222: 581597 (1991)). For various other antibody production techniques, see $Antibodies: A Laboratory Manual$, eds. Harlow et al., Cold Spring Harbor Laboratory, 1988.

In some embodiments, the term "antibody" includes an antigen-binding molecule based on a scaffold other than an immunoglobulin. For example, non-immunoglobulin scaffolds known in the art include small modular immunopharmaceuticals (see, e.g., U.S. Patent Application Publication Nos. 2008/0181892 and 2008/0227958 published Jul. 31, 2008 and Sep. 18, 2008, respectively), tetranectins, fibronectin domains (e.g., ADNECTINS®, see U.S. Patent Application Publication No. 2007/0082365, published Apr. 12, 2007), protein A, lipocalins (see, e.g., U.S. Pat. No. 7,118,915), ankyrin repeats, and thioredoxin. Molecules based on non-immunoglobulin scaffolds are generally produced by in vitro selection of libraries by phage display (see, e.g., Hoogenboom, $Method Mol. Biol.$ 178:1-37 (2002)), ribosome display (see, e.g., Hanes et al., $FEBS Lett.$ 450: 105-110 (1999) and He and Taussig, $J. Immunol. Methods$ 297:73-82 (2005)), or other techniques known in the art (see also Binz et al., $Nat. Biotech.$ 23:1257-68 (2005); Rothe et al., $FASEB J.$ 20:1599-1610 (2006); and U.S. Pat. Nos. 7,270,950; 6,518,018; and 6,281,344) to identify high-affinity binding sequences.

Antibodies can be raised against any of the suitable analytes for FGF21 protein gene expression products, described above. Numerous FGF21 antibodies are available commercially from a variety of vendors. All of these antibodies can be adapted for use in the methods provided by the invention. Antibodies for use in the methods provided by the invention can be detectably labeled (e.g., biotinylation, fluorescent, radiolabeled, et cetera) by any suitable means or may be detected indirectly, e.g., using a detectably labeled secondary antibody. In particular embodiments, the antibody is part of a kit, such as en ELISA kit, such as "Human FGF-21 Quantikine ELISA Kit" produced by R&D Systems, sold under Cat. No. DF2100.

Likewise, for measuring levels of a FGF21 nucleic acid gene expression product (e.g. in a liver biopsy or subcutaneous adipose biopsy), the level of nucleic acid FGF21 gene expression can be determined by microarray, quantitative polymerase chain reaction (qPCR), quantitative real-time polymerase chain reaction (qRTPCR), sequencing, northern blotting, digital drop PCR (ddPCR), or Southern blotting.

Suitable analytes for FGF21 nucleic acid gene expression products will be at least about 60, 65, 70, 75, 80, 85, 90, 95, 96, 97, 98, 99% or more identical (or hybridize under highly stringent hybridization conditions to a complement of a nucleic acid sequence listed in Table A) over a length of at least about 10, 20, 40, 60, 80, 100, 150, 200 or more nucleotides or over the entire length of the reference nucleic acid sequences in Table A. Fragments of the reference nucleic acid sequences in Table A—or similar nucleic acid sequences—can be of any length sufficient to distinguish the fragment from other sequences expected to be present in a mixture, e.g., at least 5, 10, 15, 20, 40, 60, 80, 100, 150, 200 or more nucleotides or at least about 5, 10, 20, 30, 40, 50, 60, 70, 80, 90, 95% of the length of the reference nucleic acid sequences in Table A.

Diagnostics

In the methods provided by the invention a subject's fructose response (monitoring dynamic levels of an FGF21 gene expression product) is typically determined after a fructose bolus and, in particular embodiments, before a fructose bolus as well, e.g. to determine a basal level of a FGF21 gene expression product. A "subject" is a mammal, including primates (e.g., humans or monkeys), cows, sheep, goats, horses, dogs, cats, rabbits, guinea pigs, rats, mice or other bovine, ovine, equine, canine, feline, rodent or murine species. Examples of suitable subjects include, but are not limited to, human patients (e.g., a human with, suspected of having, or without a disorder of metabolism, as described above). The subject can be at any stage of development, including prenatal, perinatal, infant, toddler, child, young adult, adult, middle-aged, or geriatric. In some embodiments, the subject is undergoing any known treatment for a disorder of metabolism. In certain embodiments, based on the measured fructose response, any suitable treatment for a disorder of metabolism may be indicated (or modified) based on the results of the test.

A fructose bolus is typically oral form (either a solid or liquid; in particular embodiments, a liquid solution, such as fructose diluted in water), although administration may be by any suitable means, including intravenous injection. Exemplary oral form fructose bolus include fruit or fruit juice, solutions containing free fructose that is substantially free of other saccharides (e.g. about 80, 85, 90, 95, 96, 97, 98, 99% of total saccharide is fructose), a solution comprising a mixture of fructose and glucose (e.g., about 50% of each monosaccharide, as a percentage of total carbohydrate), a solution comprising a high fructose corn syrup (e.g. 42, 55, or 90% fructose), a solution comprising sucrose or other di- or polysaccharides containing fructose, et cetera. In particular embodiments the fructose bolus is a fructose/glucose mixture, a high-fructose corn syrup, or free fructose that is substantially free of other saccharides. A fructose bolus can, in certain embodiments, comprise other molecules, such as colorants and flavorings. In certain embodiments, a fructose bolus provides about 15, 30, 35, 40, 45, 50, 55, 60, 65, 70, 75, 80, 85, 90, 95, 100, 105, 110, 115, 120, 125 grams, or more, of fructose to the subject, e.g. about 50 to about 100 grams, e.g. about 60 to about 90 grams, more particularly about 65 to about 85 grams, e.g. about 75 grams.

Levels of a FGF21 gene expression product determined after a fructose bolus are typically measured within about 4 hours, e.g., within about 5.0, 4.5, 4.0, 3.5, 3.0, 2.5, 2.0, 1.5, 1.0, 0.5 hours of the fructose bolus, e.g. within about 0.5 to about 4.0 hours, e.g. within about 2.0 hours of administering the fructose bolus.

As noted above, measuring a subject's fructose response can encompass determining a level of a FGF21 gene expression product in a time series—i.e. over time in a plurality (for example, 2, 3, 4, 5, 6, 7, 8, 9, 10) of individual measurements over the time both before (e.g., 24, 12, 6, 5, 4, 3, 2, 1, 0.5 hours before) and after (e.g., 0.5, 1, 2, 3, 4, 5, 6, 12, or 24 hours after) administering a fructose bolus.

In certain embodiments, determining a subject's fructose response—by any one of the methods provided by the invention—can be used for evaluating, inter alia, the subject's disease state (e.g. to diagnose a disorder of metabolism, based on an aberrant fructose response), the effectiveness of a treatment for a disorder of metabolism (for example, by measuring the subject's fructose response before and/or after initiating, discontinuing, or otherwise modulating a treatment for a disorder of metabolism), or to discriminate between a fructose intolerance (exhibiting an aberrant fructose response) and a gastrointestinal disorder that is not associated with fructose intolerance (not exhibiting an aberrant fructose response).

Treatment Methods

Any of the preceding methods provided by the invention can, in some embodiments, further comprise a step of implementing a therapy to treat the disorder of metabolism, e.g., based on the presence of an aberrant fructose response. Additionally, the invention provides targeted uses of any treatment for a disorder of metabolism for a subject determined to have a disorder of metabolism by a method provided by the invention (e.g., on the basis of an aberrant fructose response). That is, in some embodiments, identifying a subject with an aberrant fructose response by a method provided by the invention is an indication for initiating/implementing, discontinuing, or otherwise modifying a treatment or intervention for a disorder of metabolism.

Treatments for disorders of metabolism include ketohexokinase inhibitors (such as indazoles, see e.g. U.S. Patent Application Publication No. US 20110263559, incorporated by reference in its entirety), biguanidines (e.g. metformin), a GLP1/GLP1R agonist (such as exenatide and liraglutide), DPP-4 antagonists (e.g., saxagliptin, vildagliptin), pramlintide, insulins (e.g., glulisine, detemir, glargine, lispro, aspart), peroxisome proliferator-activated receptors (PPAR) agonists (e.g. thiazolidinediones or a fibrate (e.g. a bezafibrate, a ciprofibrate, a clofibrate (including, e.g. an etofibrate), a fenofibrate, a gemfibrozil)), an Sglt2 inhibitor (see, e.g., Canagliflozin (*J. Med. Chem.*, 2010, 53 (17), pp 6355-6360), incorporated by reference in its entirety), omega-3 or -6 fatty acids including fish oil, a ketohexokinase (fructokinase) activator, an aldolase b (Aldob) activator or inhibitor, a triokinase (dihydroxyacetone kinase 2 homolog or DAK) activator or inhibitor, a Slc2a2 (Glut2) activator or inhibitor, a Slc2a5 (Glut5) activator or inhibitor, a glucokinase (Gck) activator (see, e.g. R. Sarabu et al., Discovery of Piragliatin—First Glucokinase Activator Studied in Type 2 Diabetic Patients, *Journal of medicinal chemistry* (2012), doi: 10.1021/jm3008689; H. Ericsson et al., Tolerability, pharmacokinetics, and pharmacodynamics of the glucokinase activator AZD1656, after single ascending doses in healthy subjects during euglycemic clamp, *International journal of clinical pharmacology and therapeutics* (2012), doi: 10.5414/CP201747; G. E. Meininger et al., Effects of MK-0941, a novel glucokinase activator, on glycemic control in insulin-treated patients with type 2 diabetes, *Diabetes care* 34, 2560-6 (2011); J. Grimsby et al., Allosteric activators of glucokinase: potential role in diabetes therapy, *Science* (New York, N.Y.) 301, 370-3 (2003), all incorporated by reference in their entirety), or a glucosidase inhibitor (such as acarbose), or a Gck inhibitor, an agent that stabilizes the inhibitory interaction between Gck and Gckr, or an activator or inhibitor of other transporter or enzyme involved in fructose and/or carbohydrate metabolism, or a combination thereof. Additional treatments for a disorder of metabolism include changes in diet, exercise, or both—optionally together with changes in a treatment regime for one or more of the treatments for a disorder of metabolism discussed above.

Exemplification

Fibroblast growth factor 21 (FGF21) is a recently discovered metabolic hormone produced primarily in the liver[10,11]. FGF21 was originally described as a master regulator of the response to starvation in rodents[10,12]. However, in contrast to rodents, in human subjects, prolonged fasting has little effect on circulating FGF21 levels[13-15].

Some studies have suggested that FGF21 may be useful for the treatment of metabolic disease as administration of FGF21 to animals leads to rapid weight loss and a reduction in circulating triglycerides fatty-acids and glucose with a reduction in steatosis and improved insulin sensitivity[11,16,17.] However, FGF21 levels are elevated in obese animal models[18]. Moreover, FGF21 levels are elevated in individuals with obesity, insulin resistance, hypertriglyceridemia, NAFLD, and diabetes mellitus type 2 (DM2)[14,19-21]. Recently, FGF21 has been shown to predict the development of the metabolic syndrome and DM2 independently of obesity[22]. The mechanism accounting for the correlation between circulating FGF21 and features of the metabolic syndrome is unknown.

Carbohydrate responsive-element binding protein (ChREBP, also known as Mlx interacting protein-like or Mlxipl) is a transcription factor which is activated by products of carbohydrate metabolism and regulates the expression of glycolytic and lipogenic gene programs in an insulin-independent manner[23]. ChREBP is highly expressed in liver, adipose tissue, small intestine, and kidney[24]. The precise mechanism by which carbohydrates stimulate ChREBP transcriptional activity remains controversial[25]. Evidence points to the glucose metabolite, glucose-6-phosphate (G6P), as a key metabolite required for activation of ChREBP, although other metabolites in the glycolytic and pentose phosphate pathways have also been implicated[23,26,27].

The metabolism of fructose and glucose are different and these differences may affect how ChREBP in the liver is activated in vivo. The liver takes up 20-30% of an oral glucose load[28]. In contrast, nearly 100% of an ingested fructose load is extracted by the liver at first pass[29]. This difference is in part related to the properties of the distinct enzymes which phosphorylate glucose and fructose[30,31]. Interestingly, "catalytic" amounts of fructose markedly increase hepatic glucose uptake[32-34]. Thus, fructose ingestion may stimulate ChREBP transcriptional activity by activating hepatic glycolytic flux and the generation of G6P or other key ChREBP activating glycolytic intermediates.

Mice with whole-body deletion of ChREBP are intolerant to dietary fructose and die within several days of high-fructose feeding[24]. This demonstrates that ChREBP is essential for normal fructose metabolism. Recently, Erion and colleagues demonstrated that knocking down ChREBP in high-fructose fed rats lowers serum triglycerides and increases peripheral insulin sensitivity as measured by euglycemic-hyperinsulinemic clamps[35]. Thus, ChREBP is required for normal fructose metabolism, but may contribute the development of features of the metabolic syndrome when fructose or sugar is consumed in excess.

Figures 1A, 1B, 1C:
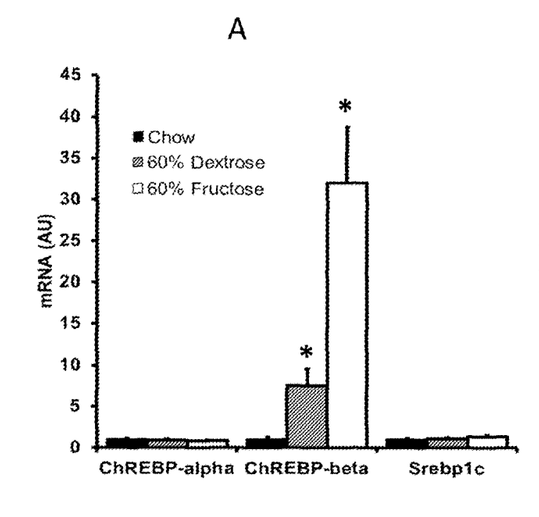
FIGS. 1A-1C are bar graphs of hepatic mRNA expression (FIG. 1A, 1B) and circulating (FIG. 1C) FGF21 levels in 15-week-old mice fed chow, 60% dextrose, or 60% fructose diets for 7 weeks, sacrificed in the ad lib fed state. * $P<0.05$ compared to all other groups. n=5-7 per group.

FGF21 expression has recently been shown to increase in liver and adipose tissue in rodents fed high-carbohydrate diets[36]. The FGF21 gene contains a ChREBP binding site in its promoter and exposure of primary hepatocytes to high glucose concentrations increases FGF21 expression in a ChREBP dependent manner[37,38]. To determine whether ChREBP might regulate circulating FGF21 levels we fed mice chow, 60% dextrose, or 60% fructose diets. Compared to chow, 7 weeks of either high-dextrose or high-fructose feeding markedly increases hepatic expression of ChREBP-β, the recently discovered novel, potent isoform of ChREBP[39] (FIG. 1A) The effect of fructose is ~3-fold greater than that of dextrose. The expression of ChREBP transcriptional targets including liver pyruvate kinase (Pklr), fatty-acid synthase (Fasn), and FGF21 also increase in high-dextrose and high-fructose diets (FIG. 1B) with a greater increase on the fructose diet. The increase in liver FGF21 expression is associated with an increase in circulating FGF21 levels, again with the highest levels found in fructose-fed mice (FIG. 1C). Thus, we hypothesized that the increase in circulating FGF21 levels associated with features of the metabolic syndrome might be due to activation of hepatic ChREBP and that fructose consumption might be important for this.

Figures 2A, 2B:
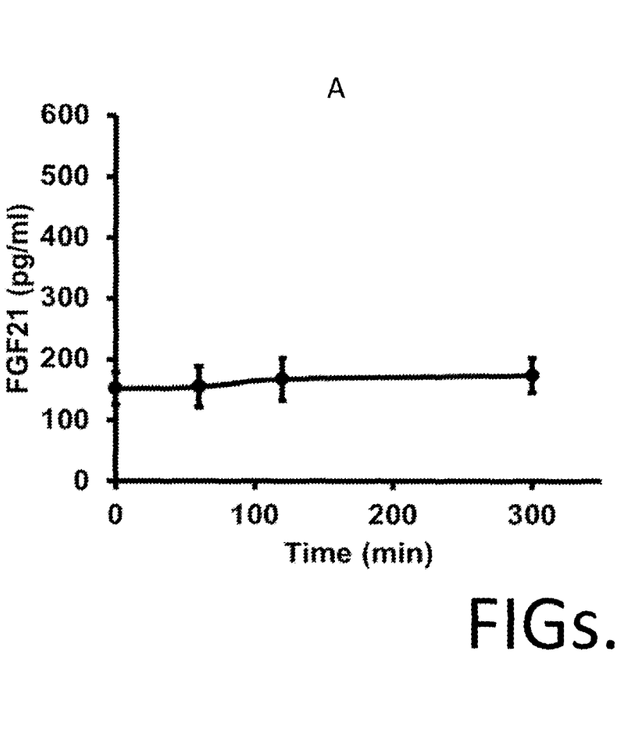

To test whether fructose ingestion can acutely regulate circulating FGF21 in human subjects, we compared the effects of administering a 75 gram oral glucose load versus a 75 gram oral fructose load on circulating FGF21 levels in lean healthy subjects. Ingestion of glucose has no effect on FGF21 levels (FIG. 2A and [14]). In contrast, circulating FGF21 levels increase ~4-fold two hours after ingestion of 75 grams of fructose (FIG. 2B). Thus oral fructose ingestion, but not glucose ingestion acutely and robustly increases circulating FGF21 levels. To our knowledge FGF21 is the only known measurable circulating biomarker that specifically assesses an individual's acute metabolic response to fructose ingestion.

Figure 3:
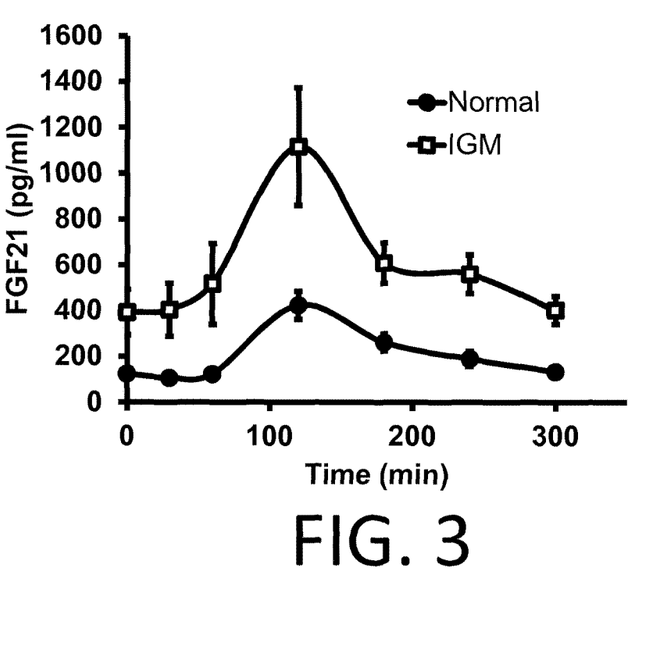
FIG. 3 is a plot of plasma FGF21 levels following ingestion of 75 grams fructose in lean, healthy human subjects (n=10) versus subjects with impaired glucose metabolism (IGM) (n=4).

We next sought to determine whether the FGF21 response to fructose ingestion can discriminate between subjects with normal glucose metabolism from those with impaired glucose metabolism. We examined the FGF21 response to fructose ingestion in 4 subjects with impaired glucose metabolism (Table 1). The baseline and FGF21 excursion following fructose ingestion is markedly higher in subjects with impaired glucose metabolism compared to healthy controls (FIG. 3). Therefore, the FGF21 response to fructose ingestion can discriminate between those with normal and impaired glucose metabolism.

TABLE 1

Baseline characteristics of lean subjects and subjects with impaired glucose tolerance who underwent fructose tolerance testing and mixed glucose + fructose tolerance testing.

|  | Lean Healthy | IGT/DM | P-value |
|---|---|---|---|
| Total | 10 | 4 |  |
| Sex (M/F) | 7/3 | 4/0 |  |
| Age (years) | 29 (24-43) | 55 (48-60) | <0.0001 |
| BMI (kg/m2) | 24.9 (21-27.6) | 33 (30.5-34.8) | 0.00045 |
| Cholesterol (mg/dl) | 176 (135-228) | 165 (122-193) | 0.5 |
| LDL | 98 (65-137) | 97 (46-122) | 0.9 |
| HDL | 59 (43-92) | 44 (34-52) | 0.07 |
| TG (mg/dl) | 94 (44-152) | 115 (60-209) | 0.5 |
| Glucose (mg/dl) during oGTT |  |  |  |
| 0 min | 83 (74-91) | 91 (78-114) | 0.1 |
| 2 hr | 97 (94-125) | 166 (135-246) | 0.002 |
| Blood pressure (mmHg) |  |  |  |
| Systolic | 119 (105-132) | 140 (134-153) | 0.006 |
| Diastolic | 75 (65-94) | 86 (64-102) | 0.15 |
| Liver enzymes (IU/L) |  |  |  |
| AST | 17 (12-21) | 20 (12-26) | 0.1 |
| ALT | 20 (9-29) | 23 (17-32) | 0.4 |

Figure 4:
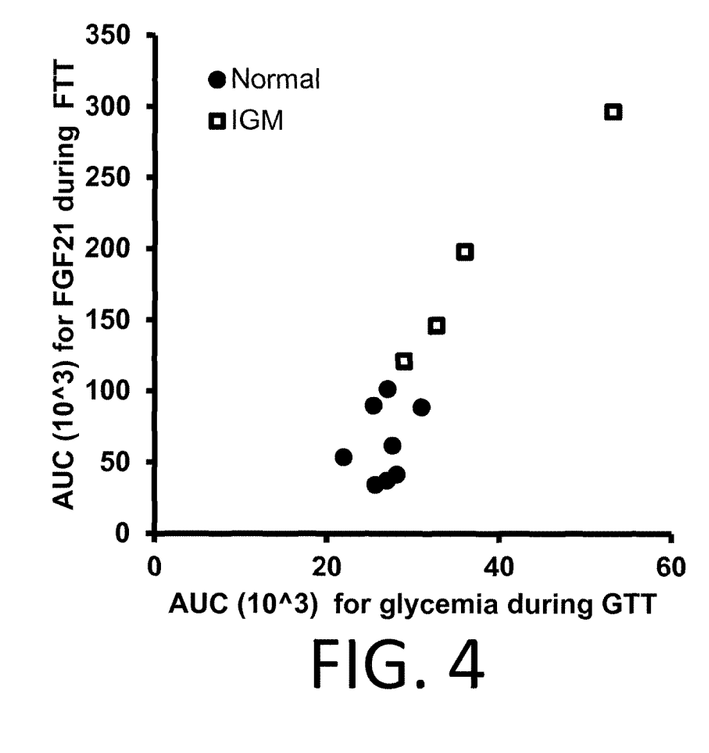
FIG. 4 is a scatterplot illustrating a correlation between glycemic area under the curve during an oral glucose tolerance test (75 grams) and FGF21 area under the curve (AUC) during an oral fructose tolerance test (75 grams). Each point represents an individual human subject. $R^2=0.85$.

To determine whether the FGF21 response to fructose might predict impaired glucose metabolism across the spectrum of glucose tolerance, we examined whether the FGF21 excursion following an oral fructose load correlates with the glucose excursion following a glucose load within an individual (FIG. 4). These dynamic responses to two distinct stimuli strongly correlate ($R^2=0.85$). This indicates that the biology that determines the FGF21 response to fructose ingestion is closely related to the biology that determines impaired glucose metabolism. As evidence noted above suggests that the FGF21 response to fructose may be mediated by activation of hepatic ChREBP, this suggests that fructose-mediated activation of hepatic ChREBP may be a key biological determinant in the development of metabolic disease.

Figure 5:
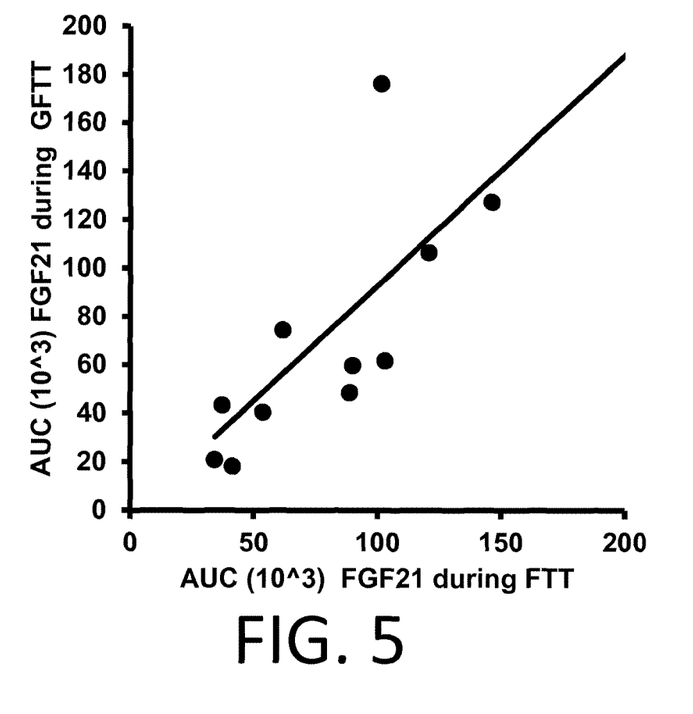
FIG. 5 is a scatterplot illustrating a correlation between FGF21 area under the curve (AUC) during a 75 gram oral fructose tolerance test (FTT) or a Mixed glucose+fructose tolerance test with 37.5 grams of each (GFTT). Each point represents an individual human subject. $R^2=0.77$.

We next compared the effects of a 75 gram fructose load to a mixture of glucose (37.5 grams) and fructose (37.5 grams) on circulating FGF21 levels. These two tests were administered a minimum of two weeks apart. There is greater than 3-fold variation in the FGF21 excursion following a fructose bolus or a glucose+fructose bolus across individuals (FIG. 5). However, the FGF21 excursion following a fructose bolus correlates highly with the excursion following a glucose+fructose bolus (FIG. 5) ($R^2$=0.77). This indicates that for an individual, the FGF21 response to fructose or combined glucose+fructose ingestion is highly reproducible. Moreover, this reproducibility suggests that genetic or chronic environmental factors such as long term diet composition and body weight rather than acute changes govern an individual's FGF21 response. Therefore, the FGF21 response to fructose ingestion will likely be an essential tool to dissect the genetics and biology of fructose metabolism and fructose-induced metabolic disease including risk for the metabolic syndrome and cardiovascular disease.

We anticipate that the FGF21 response to fructose ingestion will greatly enhance our ability to detect the development of metabolic disease early in its development. Moreover, we anticipate that this test will be useful to monitor the progression of metabolic disease and the efficacy of treatments aimed at preventing and treating metabolic disease.

1. Isomaa, B. et al. Cardiovascular morbidity and mortality associated with the metabolic syndrome. *Diabetes care* 24, 683-9 (2001).
2. Marchesini, G. et al. Nonalcoholic Fatty Liver Disease A Feature of the Metabolic Syndrome. *Diabetes* 50, 1844-1850 (2001).
3. Lakka, H.-M. H.-M. et al. The Metabolic Syndrome and Total and Cardiovascular Disease Mortality in Middle-aged Men. *JAMA: The Journal of the American Medical Association* 288, 2709-2716 (2002).
4. Haffner, S. M. et al. Prospective analysis of the insulin-resistance syndrome (syndrome X). *Diabetes* 41, 715-22 (1992).
5. Reaven, G. M. Banting lecture 1988. Role of insulin resistance in human disease. *Diabetes* 37, 1595-607 (1988).
6. Malik, V. S. et al. Sugar-sweetened beverages and risk of metabolic syndrome and type 2 diabetes: a meta-analysis. *Diabetes care* 33, 2477-83 (2010).
7. Bray, G. a Fructose and Risk of Cardiometabolic Disease. *Current atherosclerosis reports* (2012).doi:10.1007/s11883-012-0276-6
8. Stanhope, K. L. et al. Consuming fructose-sweetened, not glucose-sweetened, beverages increases visceral adiposity and lipids and decreases insulin sensitivity in overweight/obese humans. *The Journal of Clinical Investigation* 119, 1322-1334 (2009).
9. Ouyang, X. et al. Fructose consumption as a risk factor for non-alcoholic fatty liver disease. *Journal of Hepatology* 48, 993-999 (2008).
10. Badman, M. K. et al. Hepatic fibroblast growth factor 21 is regulated by PPARalpha and is a key mediator of hepatic lipid metabolism in ketotic states. *Cell metabolism* 5, 426-437 (2007).
11. Kharitonenkov, A. et al. FGF-21 as a novel metabolic regulator. *Journal of Clinical Investigation* 115, 1627-1635 (2005).
12. Inagaki, T. et al. Endocrine regulation of the fasting response by PPARalpha-mediated induction of fibroblast growth factor 21. *Cell metabolism* 5, 415-425 (2007).
13. Gälman, C. et al. The circulating metabolic regulator FGF21 is induced by prolonged fasting and PPARalpha activation in man. *Cell metabolism* 8, 169-74 (2008).
14. Dushay, J. et al. Increased Fibroblast Growth Factor 21 in Obesity and Nonalcoholic Fatty Liver Disease. *Gastroenterology* 139, 456-463 (2010).
15. Christodoulides, C., Dyson, P., Sprecher, D., Tsintzas, K. & Karpe, F. Circulating fibroblast growth factor 21 is induced by peroxisome proliferator-activated receptor agonists but not ketosis in man. *The Journal of clinical endocrinology and metabolism* 94, 3594-601 (2009).
16. Kharitonenkov, A. et al. The metabolic state of diabetic monkeys is regulated by fibroblast growth factor-21. *Endocrinology* 148, 774-781 (2007).
17. Xu, J. et al. Fibroblast Growth Factor 21 Reverses Hepatic Steatosis, Increases Energy Expenditure, and Improves Insulin Sensitivity in Diet-Induced Obese Mice. *Diabetes* 58, 250-259 (2009).
18. Fisher, F. M. et al. Obesity Is a Fibroblast Growth Factor 21 (FGF21)-Resistant State. *Diabetes* 59, 2781-2789 (2010).
19. Chavez, A. O. et al. Circulating Fibroblast Growth Factor-21 Is Elevated in Impaired Glucose Tolerance and Type 2 Diabetes and Correlates With Muscle and Hepatic Insulin Resistance. *Diabetes Care* 32, 1542-1546 (2009).
20. Li, H. et al. Fibroblast growth factor 21 levels are increased in nonalcoholic fatty liver disease patients and are correlated with hepatic triglyceride. *Journal of Hepatology* 53, 934-940 (2010).
21. Zhang, X. et al. Serum FGF21 Levels Are Increased in Obesity and Are Independently Associated With the Metabolic Syndrome in Humans. *Diabetes* 57, 1246-1253 (2008).
22. Bobbert, T. et al. Fibroblast Growth Factor 21 Predicts the Metabolic Syndrome and Diabetes Type 2 Mellitus in Caucasians. *Diabetes care* (2012).doi:10.2337/dc 12-0703
23. Uyeda, K. & Repa, J. J. Carbohydrate response element binding protein, ChREBP, a transcription factor coupling hepatic glucose utilization and lipid synthesis. *Cell metabolism* 4, 107-10 (2006).
24. Iizuka, K., Bruick, R. K., Liang, G., Horton, J. D. & Uyeda, K. Deficiency of carbohydrate response element-binding protein (ChREBP) reduces lipogenesis as well as glycolysis. *Proceedings of the National Academy of Sciences of the United States of America* 101, 7281-7286 (2004).
25. Poupeau, A. & Postic, C. Cross-regulation of hepatic glucose metabolism via ChREBP and nuclear receptors. *Biochimica et biophysica acta* 1812, 995-1006 (2011).
26. Li, M. V. et al. Glucose-6-phosphate mediates activation of the carbohydrate responsive binding protein (ChREBP). *Biochemical and biophysical research communications* 395, 395-400 (2010).
27. Arden, C. et al. Fructose 2,6-bisphosphate is essential for glucose-regulated gene transcription of glucose-6-phosphatase and other ChREBP target genes in hepatocytes. *The Biochemical journal* 443, 111-23 (2012).
28. Ludvik, B. et al. A noninvasive method to measure splanchnic glucose uptake after oral glucose administration. *The Journal of clinical investigation* 95, 2232-8 (1995).

29. Tran, C. et al. Sex differences in lipid and glucose kinetics after ingestion of an acute oral fructose load. *The British Journal of Nutrition* 1, 1-9 (2010).
30. Iynedjian, P. B. Molecular physiology of mammalian glucokinase. *Cellular and molecular life sciences: CMLS* 66, 27-42 (2009).
31. Adelman, R. C., Ballard, F. J. & Weinhouse, S. Purification and properties of rat liver fructokinase. *The Journal of biological chemistry* 242, 3360-5 (1967).
32. McGuinness, O. P. & Cherrington, A. D. Effects of fructose on hepatic glucose metabolism. *Current Opinion in Clinical Nutrition and Metabolic Care* 6, 441-448 (2003).
33. Petersen, K. F., Laurent, D., Yu, C., Cline, G. W. & Shulman, G. I. Stimulating effects of low-dose fructose on insulin-stimulated hepatic glycogen synthesis in humans. *Diabetes* 50, 1263-8 (2001).
34. Agius, L. Glucokinase and molecular aspects of liver glycogen metabolism. *The Biochemical journal* 414, 1-18 (2008).
35. Erion, D. M. et al. The Role of the Carbohydrate Response Element-Binding Protein in Male Fructose-Fed Rats. 154, 36-44 (2013).
36. Sánchez, J., Palou, A. & Picó, C. Response to Carbohydrate and Fat Refeeding in the Expression of Genes Involved in Nutrient Partitioning and Metabolism: Striking Effects on Fibroblast Growth Factor-21 Induction. *Endocrinology* 283, 21988-21996 (2009).
37. Ma, L., Robinson, L. N. & Towle, H. C. ChREBP•Mlx Is the Principal Mediator of Glucose-induced Gene Expression in the Liver. *Journal of Biological Chemistry* 281, 28721-28730 (2006).
38. Iizuka, K., Takeda, J. & Horikawa, Y. Glucose induces FGF21 mRNA expression through ChREBP activation in rat hepatocytes. *FEBS Letters* 583, 2882-2886 (2009).
39. Herman, M. A. et al. A novel ChREBP isoform in adipose tissue regulates systemic glucose metabolism. *Nature* 484, 333-8 (2012).

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences disclosed in this application, such as GeneIDs, Unigene IDs, or HomoloGene ID, or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g. Pub Chem compound, Pub Chem substance, or Pub Chem Bioassay entries, including the annotations therein, such as structures and assays et cetera) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g. elements, including numerical ranges and exemplary embodiments) of particular embodiments and aspects of the invention including the working examples. For example, particular experimental parameters exemplified in the working examples can be adapted for use in the methods provided by the invention piecemeal without departing from the invention. For example, for materials that are disclosed or used in the methods provided by the invention, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

What is claimed is:

1. A method of detecting a fructose response in a subject, comprising:
    determining a level of a fibroblast growth factor 21 (FGF21) protein gene expression product in an isolated blood sample obtained from the subject, or a fraction thereof, wherein:
    the subject was administered a fructose bolus comprising from about 20 grams to about 100 grams of fructose;
    the level of the FGF21 protein gene expression product is determined within about five hours after the fructose bolus; and
    the determined level of the FGF21 protein gene expression product is the subject's fructose response.

2. The method of claim 1, wherein the level of FGF21 protein gene expression product is determined by ELISA, Western Blotting, RIA (radioimmunoassay), HPLC (high precision liquid chromatography), SPR (surface plasmon resonance), SAT (suspension array technology), direct peptide sequencing, or mass spectrometry.

3. The method of claim 1, wherein the subject is undergoing treatment with a ketohexokinase inhibitor, a biguanidine, a GLP1/GLP1R agonist, a peroxisome proliferator-activated receptors (PPAR) agonist, an Sglt2 inhibitor, an omega-3 fatty acid, an omega-6 fatty acid, a ketohexokinase (fructokinase) activator, an aldolase b (Aldob) activator, an aldolase b (Aldob) inhibitor, a triokinase activator, a triokinase inhibitor, a Slc2a2 (Glut2) activator, a Slc2a2 (Glut2) inhibitor, a Slc2a5 (Glut5) activator, a Slc2a5 (Glut5) inhibitor, a glucokinase (Gck) activator, a Gck inhibitor, an agent that stabilizes the inhibitory interaction between Gck and Gckr, a glucosidase inhibitor, an activator of a transporter or enzyme involved in fructose or carbohydrate metabolism, an inhibitor of a transporter or enzyme involved in fructose or carbohydrate metabolism, or a combination thereof.

4. The method of claim 1, wherein the level of a FGF21 protein gene expression product is determined within about 0.5 to about 4 hours after administering the fructose bolus.

5. The method of claim 1, further comprising determining a level of the FGF21 protein gene expression product before administering the fructose bolus.

6. The method of claim 5, wherein determining a level of a FGF21 protein gene expression product comprises determining a level of a FGF21 protein gene expression product in at least 2, 3, 4, or 5 individual isolated blood samples, or fractions thereof, obtained from the subject over a period of time within about five hours after the fructose bolus.

7. A method of detecting a fructose response in a subject, comprising:
 administering a fructose bolus comprising from about 20 grams to about 100 grams of fructose to the subject; and
 determining a level of a fibroblast growth factor 21 (FGF21) protein gene expression product in an isolated serum sample obtained from the subject, wherein:
 the level of the FGF21 protein gene expression product is measured about 0.5 to about 4 hours after administering the fructose bolus, and
 a basal level of FGF21 protein gene expression product in an isolated serum sample obtained from the subject was determined before administering the fructose bolus to the subject.

* * * * *